United States Patent [19]

Sano et al.

[11] Patent Number: 5,231,116
[45] Date of Patent: Jul. 27, 1993

[54] HYDROPHILIC URETHANE PREPOLYMER COMPOSITION

[75] Inventors: Takashi Sano, Otsu; Hidehiro Uchikata, Kameoka, both of Japan

[73] Assignee: Dai-Ichi Kogyo Seiyaku Co., Ltd., Kyoto, Japan

[21] Appl. No.: 733,543

[22] Filed: Jul. 22, 1991

[30] Foreign Application Priority Data

Jul. 23, 1990 [JP] Japan .................................. 2-194215

[51] Int. Cl.$^5$ ...................... C08G 18/77; C08G 18/10; C08G 18/12; C07C 269/02
[52] U.S. Cl. .................................... 521/159; 521/160; 521/174; 521/905; 560/158; 528/59; 528/77; 528/904
[58] Field of Search .................. 560/26, 158; 521/159, 521/160, 174, 905; 528/59, 77

[56] References Cited

U.S. PATENT DOCUMENTS

| | | | |
|---|---|---|---|
| 3,218,348 | 11/1965 | McElroy et al. | 560/26 |
| 3,883,577 | 5/1975 | Rabizzoni et al. | 560/26 |
| 4,061,662 | 12/1977 | Marans et al. | 560/26 |
| 4,137,200 | 1/1979 | Wood et al. | 521/159 |
| 4,202,956 | 5/1980 | Taylor | 560/26 |
| 4,940,737 | 7/1990 | Braatz et al. | 521/159 |
| 5,164,421 | 11/1992 | Kiamil et al. | 528/59 |

FOREIGN PATENT DOCUMENTS

| | | | |
|---|---|---|---|
| 0392788 | 4/1989 | European Pat. Off. | 560/26 |
| 2261816 | 4/1989 | Japan | 560/26 |
| 8905319 | 6/1989 | World Int. Prop. O. | 528/77 |

OTHER PUBLICATIONS

Kirk-Othmer, *Encyclopedia of Chemical Technology*, vol. 18, pp. 638-641 (1986).

*Primary Examiner*—José G. Dees
*Assistant Examiner*—B. Frazier
*Attorney, Agent, or Firm*—Millen, White, Zelano & Branigan

[57] ABSTRACT

A urethane prepolymer composition useful as sealant is disclosed. The composition comprises a reaction product of an organic polyisocyanate and a polyether polyol mixture at an NCO/OH equivalent ratio from 1.6 to 2.5. The polyether polyol mixture contains (a) from 75 to 95 % by weight of the mixture of a polyoxyalkylenediol having an average MW from 400 to 1,000 and an oxyethlene unit content greater than 50 % by weight, and (b) the balance of the mixture of a polyoxyalkylenetriol having an average MW from 5,000 to 10,000 and an oxyethylene unit content greater than 50 % by weight. An equivalent composition is produced by reacting the polyoxyalkylenediol and polyoxyalkylenetriol with the organic polyisocyanate separately and mixing together after the reaction.

14 Claims, No Drawings

HYDROPHILIC URETHANE PREPOLYMER COMPOSITION

BACKGROUND OF THE INVENTION

This invention relates to a hydrophilic urethane prepolymer composition useful, for example, as a sealant.

Urethane prepolymers used for sealing purposes must be uniformly dispersible in water and capable of forming nonshrinkable, resilient, and mechanically strong cured products having a cellular structure by the reaction with water. Hydrophilic urethane prepolymers have been used, utilizing these properties, for ground-accretion and wet wood-gluing purposes as well.

Japanese Patent Publication No. 25205/73 discloses a hydrophilic urethane prepolymer produced by reacting polyethylene glycol with an organic polyisocyanate. Japanese Patent Publication No. 19846/78 discloses a hydrophilic urethane prepolymer produced by reacting an organic polyisocyanate with a random or block copolymer of ethylene oxide and propylene oxide having an oxyethylene unit content greater than 50% by weight. Foam-forming hydrophilic urethane prepolymers are disclosed in Japanese Patent Kokai No. 47969/76, U.S. Pat. Nos. 3,894,131 and 3,985,688. They are mixtures of urethane prepolymers derived from polyethylene glycol having an MW of 850-1,000 and from polyethylene glycol having an MW of 1,250-1,550, the average MW of polyethylene glycol being 1,000-1,300.

The foam-forming hydrophilic prepolymers are advantageous in that, when injected into leaking sites in conjunction with water, the resulting foamed polyurethane mass is forced even into very fine spaces by the pressure of the carbon dioxide gas evolved by the reaction of isocyanate groups with water.

However, the prior art hydrophilic urethane prepolymers suffer from certain shortcomings. They tend to produce a foam having a relatively coarse cell texture. It is for this reason that some of previously cited patents teach the use of a surfactant to stabilize the foam but its efficacy has been proven to be not satisfactory. Furthermore, the foam produced from the prior art prepolymers are subject to shrinkage or compression because of their open cell structure. When this occurs, the polyurethane sealing layer peels from the concrete surfaces against which it seals so that it fails to perform the desired sealing function.

Accordingly, it is a principal object of this invention to provide a hydrophilic urethane prepolymer composition which is easily dispersible in water and capable of producing a non-shrinkable, closed cell type polyurethane foam having a fine cell texture and improved mechanical strength and elasticity.

SUMMARY OF THE INVENTION

According to this invention, the above and other objects may be accomplished by providing a hydrophilic urethane prepolymer composition comprising a reaction product of an organic polyisocyanate and a polyol component at an NCO/OH equivalent ratio from 1.6 to 2.5; said polyol component being a mixture of (a) from 75 to 95% by weight of the mixture of a polyoxyalkylenediol having an average molecular weight from 400 to 1,000 and an oxyethylene unit content greater than 50% by weight, and (b) the balance of the mixture of a polyoxyalkylenetriol having an average molecular weight from 5,000 to 10,000 and an oxyethylene unit content greater than 50% by weight.

According to another aspect of the present invention, there is provided a hydrophilic urethane prepolymer composition comprising a mixture of (a) from 81 to 97% by weight of the mixture of a reaction product of an organic polyisocyanate and a polyoxyalkylenediol at an NCO/OH equivalent ratio from 1.6 to 2.5, said polyoxyalkylenediol having an average molecular weight from 400 to 1,000 and an oxyethylene unit content greater than 50% by weight; and (b) the balance of the mixture of a reaction product of an organic polyisocyanate and a polyoxyalkylenetriol at an NCO/OH equivalent ratio from 1.6 to 2.5, said polyoxyalkylenetriol having an average molecular weight from 5,000 to 10,000 and an oxyethylene unit content greater than 50% by weight.

DETAILED DISCUSSION

Two types of polyether polyol components are used in the hydrophilic urethane prepolymer composition of the present invention. The first is a polyoxyalkylenediol having an average molecular weight from 400 to 1,000 and an oxyethylene unit content greater than 50% by weight (hereinafter referred to as the "first polyol"), and the second is a polyoxyalkylenetriol having an average molecular weight from 5,000 to 10,000 and an oxyethylene unit content greater than the 50% by weight (hereinafter referred to as the "second polyol").

The first polyol should have an average molecular weight and oxyethylene unit content within the range as defined in order that the prepolymer composition is easily dispersible in water and that the polyurethane foam produced from the prepolymer composition will have a relatively high mechanical and adhesion strength. Polyethylene glycols having a molecular weight within the defined range are preferably employed.

The second polyol is incorporated into the prepolymer composition for imparting the polyurethane foam with a hardly shrinkable, fine closed cell-texture.

The first and second polyols may contain less than 50% by weight of an oxyalkylene unit other than the oxyethylene unit. To this end, the polyols are produced by copolymerizing ethylene oxide with propylene oxide, 1,2-butylene oxide, 2,3-butylene oxide or the like.

The first and second polyols may be mixed either before their reaction with an organic polyisocyanate to produce a premix prepolymer or after having reacted with the polyisocyanate to produce a postmix prepolymer. Although it is believed that the precise constituents of the premix prepolymer differ and the postmix prepolymer, they function in substantially the same manner and produce substantially the same result provided that the NCO content of the premix and post-mix prepolymers are about the same. Thus, 75–95% weight % of the first polyol in the polyol premix generally corresponds to 81–97 weight % of the prepolymer solely derived from the first polyol present in the post-mix prepolymer.

Any commercially available organic polyisocyanate may be used. Examples thereof include 2,4-tolylenediisocyanate, 2,6-tolylenediisocyanate, mixtures thereof such as TDI-80 and TDI-65, diphenylmethanediisocyanate (MDI), liquid MDI, polymeric MDI, hexamethylenediisocyanate, xylylenediisocyanate, isophoronediisocyanate, hydrogenated MDI and the like. Tolylenediisocyanate is preferable.

The reaction between the polyetherpolyols and the polyisocyanates are well-known. To produce urethane prepolymers having a plurality of terminal free isocyanate groups, the NCO/OH equivalent ratio should be from 1.6 to 2.5. If the NCO/OH ratio is too low, the prepolymer will have a high viscosity making the workability and water-dispersibility of the prepolymer unsatisfactory. Conversely, if the NCO/OH ratio is too high, not only does the prepolymer contains a large amount of hazardous free isocyanate monomers but also the resulting foam will become brittle.

The hydrophilic urethane prepolymer composition of the present invention may contain an organic solvent free from active hydrogen atoms to adjust the viscosity and water-dispersibility of the composition to an optimal level. Examples thereof include ketones such as acetone and methyl ethyl ketone; esters such as ethyl acetate and butyl acetate; and halogenated hydrocarbons such as methylene chloride, 1,1,1-trichloroethane and trichloroethylene.

The hydrophilic urethane prepolymer composition of the present invention may contain a conventional catalyst such as dibutyltin dilaurate, dibutyltin diacetate, triethylenediamine, triethylamine and the like.

The hydrophilic urethane prepolymer composition of the present invention can be converted to a non-shrinkable, closed cell type polyurethane foam having a fine cell texture and a good mechanical strength and elasticity by containing well-balanced proportions of the first and second polyols.

The invention is further illustrated by the following examples in which all parts and percents are by weight unless otherwise specified.

EXAMPLE 1

A one liter flask was charged with 489 parts of polyethylene glycol having an average MW of 600 and 86 parts of polyoxyethylenetriol having an average MW of 7,700. Then 275 parts (NCO/OH = 1.9) of tolylenediisocyanate were added and allowed to react at 80° C. for 90 minutes. After the reaction, the reaction product was cooled to 30° C. and diluted with 150 parts of acetone to obtain a hydrophilic urethane prepolymer composition having a free NCO content of 6.3% and a viscosity of 560 cP at 20° C.

EXAMPLE 2

Analogous to Example 1, a mixture of 530 parts of polyethylene glycol having an average MW of 700 and 59 parts of polyoxyethylenetriol having an average MW of 7,700 was reacted with 261 parts of TDI at an NCO/OH ratio of 1.96. The reaction product was diluted with 150 parts of acetone to obtain a hydrophilic urethane prepolymer composition having a free NCO content of 6.1% and a viscosity of 610 cP at 20° C.

EXAMPLE 3

Analogous to Example 1, a mixture of 159 parts of polyethylene glycol having an average molecular weight of 1,000, 371 parts of polyethylene glycol having an average molecular weight of 600, and 59 parts of polyoxyethyleneoxypropylenetriol having an average MW of 7,700 was reacted with 261 parts of TDI at an NCO/OH ratio of 1.88. The reaction product was diluted with 150 parts of acetone to obtain a hydrophilic urethane prepolymer composition having a free NCO content of 5.7% and a viscosity of 680 cP at 20° C.

COMPARATIVE EXAMPLE 1

Analogous to Example 1, a mixture of 297 parts of polyethylene glycol having an average MW of 1,000 and 297 parts of polyethylene glycol having an average MW of 600 was reacted with 256 parts of TDI at an NCO/OH ratio of 1.83. The reaction product was diluted with 150 parts of acetone to obtain a hydrophilic urethane prepolymer having a free NCO content of 5.1% and a viscosity of 720 cP at 20° C.

COMPARATIVE EXAMPLE 2

Analogous to Example 1, a mixture of 487 parts of polyethylene glycol having an average molecular weight of 600 and 86 parts of polyoxyethylenediol having an average molecular weight of 3,000 were reacted with 277 parts of TDI at an NCO/OH ratio of 1.9. The reaction product was diluted with 150 parts of acetone to obtain a hydrophilic urethane prepolymer composition having a free NCO content of 6.3% and a viscosity of 550 cP at 20° C.

Foaming Test

Hydrophilic urethane prepolymer compositions of Examples 1–3 and Comparative Examples 1–2 were reacted with equal parts of water and the resulting foam was evaluated. The results are shown in Table 1.

TABLE 1

| Test items | Compositions | | | | |
| --- | --- | --- | --- | --- | --- |
|  | Ex. 1 | Ex. 2 | Ex. 3 | Comparative Ex. 1 | Comparative Ex. 2 |
| Water-dispersibility | Good | Good | Good | Dispersible with vigorous stirring | Good |
| Times of foamed volume | 7.5 | 7.3 | 7.0 | 5.1 | 6.7 |
| Elasticity | Good | Good | Good | Not measurable due to shrink | Not measurable due to shrink |
| Strength | Good | Good | Good | Brittle | Fair |
| Cell size | Very fine | Very fine | Very fine | Coarse | Fine |
| Shrink after drying | No | No | No | Yes | Yes |
| Overall judgment as sealant | Best | Best | Best | Not usable | Not usable |

EXAMPLE 4

645 parts of polyethylene glycol having an average molecular weight of 600 were reacted with 355 parts of TDI at a NCO/OH ratio of 1.95 to obtain Prepolymer No. 1 having a free NCO content of 6.0%.

936 parts of polyoxyalkylenetriol having an average molecular weight of 7,700 produced by addition polymerizing a 80:20 mixture of ethylene oxide and propylene oxide starting from glycerine were reacted with 64 parts of TDI at an NCO/OH ratio of 2.00 to obtain prepolymer No. 4 having a free NCO content of 2.52%.

90 parts of Prepolymer No. 1 and 10 parts of Prepolymer No. 4 were mixed together in 30 parts of acetone to give a hydrophilic urethane prepolymer composition having a free NCO content of 5.7% and a viscosity of 550 cP at 20° C.

EXAMPLE 5

674 parts of polyethylene glycol having an average molecular weight of 700 were reacted with 326 parts of TDI at an NCO/OH ratio of 1.95 to obtain Prepolymer No. 2 having a free NCO content of 7.7%.

90 parts of Prepolymer No. 2 and 10 parts of Prepolymer No. 4 produced in Example 4 were mixed together in 20 parts of acetone to give a hydrophilic urethane prepolymer composition having a free isocyanate content of 5.9% and a viscosity of 620 cP.

EXAMPLE 6

95 parts of Prepolymer No. 2 produced in Example 5 and 5 parts of Prepolymer No. 4 produced in Example 4 were mixed together in 20 parts of acetone to give a hydrophilic urethane prepolymer composition having a free NCO content of 6.2% and a viscosity of 690 cP at 20° C.

COMPARATIVE EXAMPLE 3

747 parts of polyethylene glycol having an average MW of 1,000 were reacted with 253 parts of TDI at an NCO/OH ratio of 1.95 to obtain Prepolymer No. 3 having a free NCO content of 6.0%.

60 parts of Prepolymer No. 3 and 40 parts of Prepolymer No. 1 produced in Example 4 were mixed together in 20 parts of acetone to give a hydrophilic urethane prepolymer composition having an NCO content of 5.7% and a viscosity of 610 cP at 20° C.

COMPARATIVE EXAMPLE 4

896 parts of polyoxyalkylenediol having an average MW of 3,000 produced by addition polymerizing a 80:20 mixture of ethylene oxide and propylene oxide starting from propylene glycol were reacted with 104 parts of TDI at an NCO/OH ratio of 2.0 to obtain Prepolymer No. 5 having a free NCO content of 2.52%.

90 parts of Prepolymer No. 2 produced in Example 5 and 10 parts of Prepolymer No. 5 were mixed together in 20 parts of acetone to give a hydrophilic urethane prepolymer composition having a free NCO content of 6.0% and a viscosity of 650 cP at 20° C.

Foaming Test

Hydrophilic urethane Prepolymer compositions of Examples 4–6 and Comparative Examples 3–4 were reacted with equal parts of water and the resulting foam was evaluated. The results are shown in Table 2.

TABLE 2

| Test items | Compositions | | | | |
| --- | --- | --- | --- | --- | --- |
| | Ex. 4 | Ex. 5 | Ex. 6 | Comparative Ex. 3 | Comparative Ex. 4 |
| Water-dispersibility | Good | Good | Good | Dispersible with vigorous stirring | Fair |
| Times of foamed volume | 6.8 | 7.1 | 7.5 | 4.5 | 6.1 |
| Elasticity | Good | Good | Good | Not measurable due to shrink | Not measurable due to shrink |
| Strength | Good | Good | Good | Not measurable due to shrink | Not measurable due to shrink |
| Cell size | Very fine | Very fine | Very fine | Coarse | Fine |
| Shrink after drying | No | No | No | Shrink after 6 hrs. | Shrink after 24 hrs. |
| Overall judgment as sealant | Best | Best | Best | Not usable | Not usable |

We claim:

1. A hydrophilic urethane prepolymer composition comprising a reaction product of an organic polyisocyanate and a polyol component at an NCO/OH equivalent ratio from 1.6 to 2.5; said polyol component being a mixture of (a) from 75 to 95% by weight of the mixture of a polyoxyalkylenediol having an average molecular weight from 400 to 1,000 and an oxyethylene unit content of greater than 50% by weight, and (b) the balance of the mixture of a polyoxyalkylenetriol having an average molecular weight from 5,000 to 10,000 and an oxyethylene unit content greater than 50% by weight.

2. The hydrophilic urethane prepolymer composition according to claim 1, wherein said organic polyisocyanate is tolylenediisocyanate.

3. The hydrophilic urethane prepolymer composition according to claim 2, wherein said polyoxyalkylenediol is a polyethylene glycol.

4. The hydrophilic urethane prepolymer composition according to claim 1, wherein said polyoxyalkylenetriol is a poly(oxyethyleneoxypropylene)triol.

5. A hydrophilic urethane prepolymer composition comprising a mixture of (a) from 81 to 97% by weight of the mixture of a reaction product of an organic polyisocyanate and a polyoxyalkylenediol at an NCO/OH equivalent ratio from 1.6 to 2.5, said polyoxyalkylenediol having an average molecular weight from 400 to 1,000 and an oxyethylene unit content greater than 50% by weight; and (b) the balance of the mixture of a reaction product of an organic polyisocyanate and a polyoxyalkylenetriol at an NCO/OH ratio from 1.6 to 2.5, said polyoxyalkylenetriol having an average molecular weight from 5,000 to 10,000 and an oxyethylene unit content greater than 50% by weight.

6. The hydrophilic urethane prepolymer composition according to claim 5, wherein said organic polyisocyanate is tolylenediisocyanate.

7. The hydrophilic urethane prepolymer composition according to claim 5, wherein said polyoxyethylenediol is a polyethylene glycol.

8. The hydrophilic urethane prepolymer composition of claim 5, wherein said polyoxyalkylenetriol is a poly(oxyethyleneoxypropylene)triol.

9. The hydrophilic urethane prepolymer composition according to claim 1 further comprising an organic solvent free from active hydrogen atoms.

10. The hydrophilic urethane prepolymer composition according to claim 5 further comprising an organic solvent free from active hydrogen atoms.

11. The hydrophilic urethane prepolymer composition according to claim 5, wherein said organic polyisocyanate is tolylenediisocyanate; wherein said polyoxyethylenediol is a polyethylene glycol; and wherein said polyoxyalkylenetriol is a poly(oxyethyleneoxypropylene)triol.

12. A stable elastic polyurethane foam produced by mixing a urethane prepolymer composition according to claim 9 with water.

13. A stable elastic polyurethane foam produced by mixing a urethane prepolymer composition according to claim 10 with water.

14. The stable elastic polyurethane foam according to claim 13, wherein said organic polyisocyanate is tolylenediisocyanate; wherein said polyoxyethylenediol is a polyethylene glycol; and wherein said polyoxyalkylenetriol is a poly(oxyethyleneoxypropylene)triol.

* * * * *